United States Patent [19]

Neal

[11] Patent Number: 4,911,178
[45] Date of Patent: Mar. 27, 1990

[54] PACEMAKER WIRE DRESSING

[76] Inventor: Carol A. Neal, 1804 Heriford Rd., Columbia, Mo. 65202

[21] Appl. No.: 201,534

[22] Filed: Jun. 2, 1988

[51] Int. Cl.$^4$ .............................................. A61N 1/00
[52] U.S. Cl. ...................................... 128/802; 604/174; 150/131
[58] Field of Search ................... 128/419 P, 639, 802, 128/854; 604/174, 179, 180; 600/16; 150/131, 132, 143

[56] References Cited

U.S. PATENT DOCUMENTS

| | | | |
|---|---|---|---|
| 3,685,645 | 8/1972 | Kawaguchi | 128/419 D |
| 3,728,839 | 4/1973 | Glick | 53/449 |
| 3,940,873 | 3/1976 | Lawless | 150/52 R |
| 4,013,081 | 3/1977 | Kolenik | 128/419 P |
| 4,114,352 | 9/1978 | Horton et al. | 128/639 |
| 4,276,882 | 7/1981 | Dickhudt | 128/419 P |
| 4,332,338 | 6/1982 | Christiansen | 150/143 |
| 4,582,508 | 4/1986 | Pavelka | 604/179 |
| 4,666,432 | 5/1987 | McNeish et al. | 604/174 |
| 4,738,661 | 4/1988 | Marut | 604/179 |

FOREIGN PATENT DOCUMENTS

| | | | |
|---|---|---|---|
| 1118357 | 6/1956 | France | 150/132 |
| 2554713 | 5/1985 | France | 604/174 |

Primary Examiner—Max Hindenburg
Assistant Examiner—Kennedy Schaetzle
Attorney, Agent, or Firm—Litman, McMahon & Brown

[57] ABSTRACT

A surgical dressing used to separate and hold electrical leads or wires is disclosed. Following heart surgery, negative and positive electrical leads may be attached to a patient's heart in pairs and left protruding from an incision or incisions in the patient's chest so the patient's heartbeat can be stabilized by external means without reopening the patient's chest. These electrical leads are wrapped around themselves by medical personnel but frequently become tangled and must be separated before they can be attached to a pacemaker machine in an emergency. The dressing disclosed is a booklet which uses compartments in the form of pockets or pages for receiving the electrical leads and holding them in a tangle-free, separated condition for easy, rapid access and use in an emergency.

7 Claims, 2 Drawing Sheets

PACEMAKER WIRE DRESSING

BACKGROUND OF THE INVENTION

This invention relates to surgical dressings and, more particularly, to surgical dressings in the form of booklets made to carry the electrical leads of a pacemaker tucked into pockets formed by pages of the booklet or wrapped around notches disposed in the ends of the booklet pages so that such leads are separated by the pages of the booklet and remain tangle free and available for rapid insertion into a mechanical device to stabilize a faltering or accelerating heartbeat following surgery, and more particularly, heart surgery.

At the present time following open heart surgery, electrical leads will be surgically attached to a patient's heart and left protruding from an opening in the patient's chest so that such leads can be inserted into a pacemaker or monitoring machine if the patient's heartbeat is fibrillating or faltering so that external means can be used to stabilize the heartbeat without resort to additional surgery to reopen the chest cavity. Typically, each opening in a patient's chest will carry both a positive and a negative wire, and incisions might be made under each rib cavity so that a patient would have four wires dangling from his or her chest. Such leads are inconvenient and unsightly and frequently tangle or pull. They may require manual separation if it becomes necessary to attach the leads to a pacemaker machine.

The present invention responds to the disadvantages set forth above by employing a dressing in booklet form which receives and separates the negative and positive wires protruding from the patient's chest and stores them in pockets formed by the pages of the dressing or, alternatively, by coiling them around notched pages of the dressing so the leads are neatly separated and quickly inserted into the negative and positive receptacles of a pacemaker machine.

Additionally, the dressing of the present invention is easy to assemble and requires a minimum of labor, thereby making the dressings inexpensive to manufacture and dispose after use.

OBJECTS OF THE INVENTION

It is, therefore, the primary object of this invention to provide a surgical dressing which is neat in appearance and offers an answer to the dangling pacemaker wires heretofore a familiar result of heart surgery.

It is a further object of this invention to provide a surgical dressing which separates the wires extending from the chest cavity and keeps them available in pockets or pages for immediate access and insertion into a pacemaker receptable.

A more particular object of this invention is to provide a surgical dressing, as aforesaid, which is lightweight and convenient to use and fasten, yet renders the pacemaker wires readily accessible and is disposable after use.

Another object of this invention is to provide a dressing, as aforesaid, wherein the pages of the dressing are collapsibly stacked upon closure of the booklet, so the booklet can be secured at the open end by means of a fastener, to ensure capture of the coiled wires.

Yet another object of this invention is to provide a dressing, as aforesaid, wherein the dressing is made of inexpensive material such as cheese cloth or gauze fabric, and employs hem stitching around the edges thereof to prevent raveling yet reduce cost of manufacture so that the dressings are readily disposable and can be discarded after use by a patient.

DESCRIPTION OF THE PREFERRED EMBODIMENT

Figure 1:
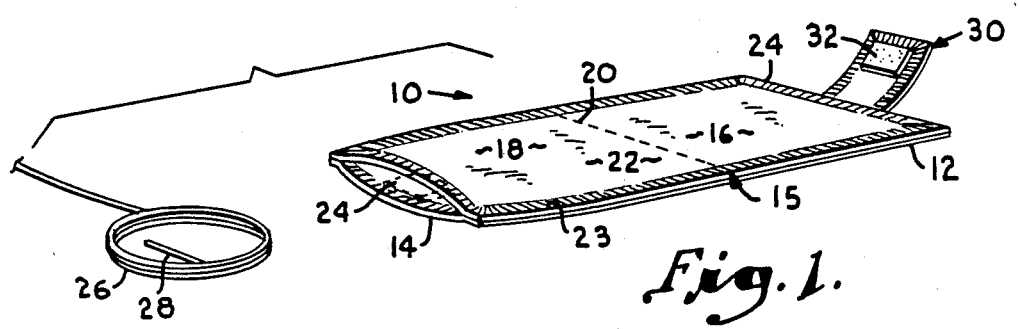
FIG. 1 is a perspective view of the preferred embodiment of the invention, showing the center stitching separating the two compartments or pages of the dressing booklet and the coiled pacemaker wire shown to the left in removed position.

Referring to the drawings, FIG. 1 shows a booklet dressing 10 with the outer cover pages 12 and 14 in a flat position. The inner pages 16 and 18 are divided by a line of fold 20 formed by stitching through the middle of the double thickness of rectangular piece 22 laid on top of rectangular piece 15. The combined pieces are then bound together at the top and bottom edges of pieces 15 and 22 with stitching 23 to form pockets or compartments 24 accessible from the outer or short sides 25 of the booklet dressing 10.

A coiled pacemaker wire 26 is shown in FIG. 1 to the left of the dressing 10 in removed position with the lead or probe 28 visible inside the coil.

Figure 2:
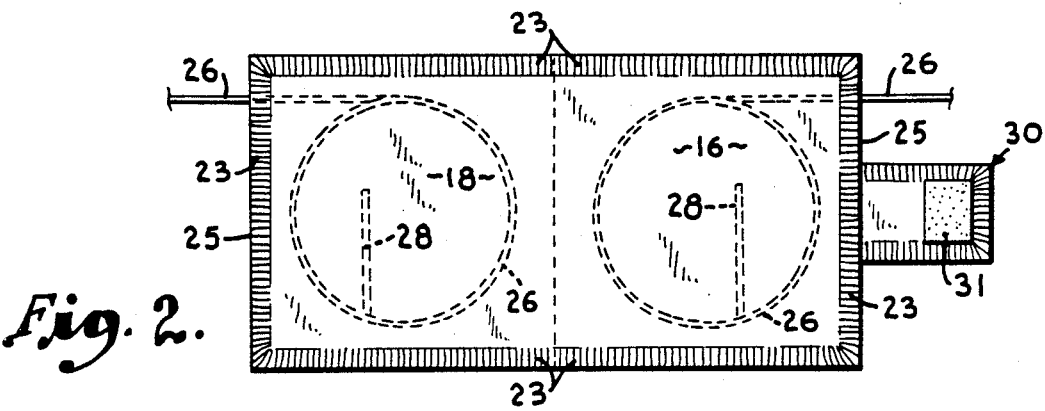
FIG. 2 is a top plan view of the embodiment of FIG. 1 with the center divider shown and the coiled pacemaker wires and their probes shown thereon in broken or phantom lines.

The separation of the sandwiched rectangular pieces 15 and 22 is further demonstrated in FIG. 2 where negative and positive pacemaker wires 26 are shown within the pockets 24 by use of phantom or broken lines.

The fastener 30 that closes the booklet 10 is shown in FIG. 2 extending from the right of the righthand compartment or pocket 24. velcro fastener 32 can be used at the end of fastener 30 as the preferred closure means although any other simple, low-cost means of closure could be used.

Figure 3:
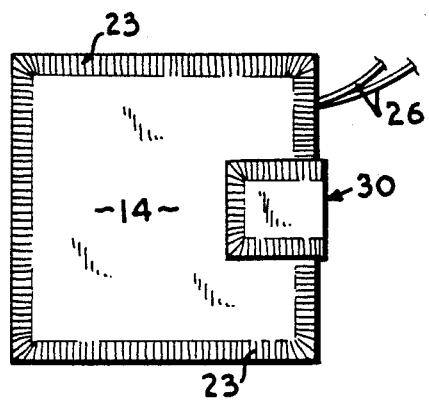
FIG. 3 is a top plan view of the dressing closed left to right with the fastener in place and the pacemaker wires enclosed in the envelope with their ends visible at the top right of the closed dressing.

When the compartments 24 of the dressing 10 shown in FIG. 2 are folded left to right with the coiled wires 26 therein, the closed booklet 10 is as shown in FIG. 3. Although FIG. 3 shows the wires 26 extending from the same corner, in actual use it would be preferred that the wires 26 be coiled so that the leads 26 are separated by the fastener 30 for ease of connection, but the details of separation can be dictated by the user.

Figure 4:
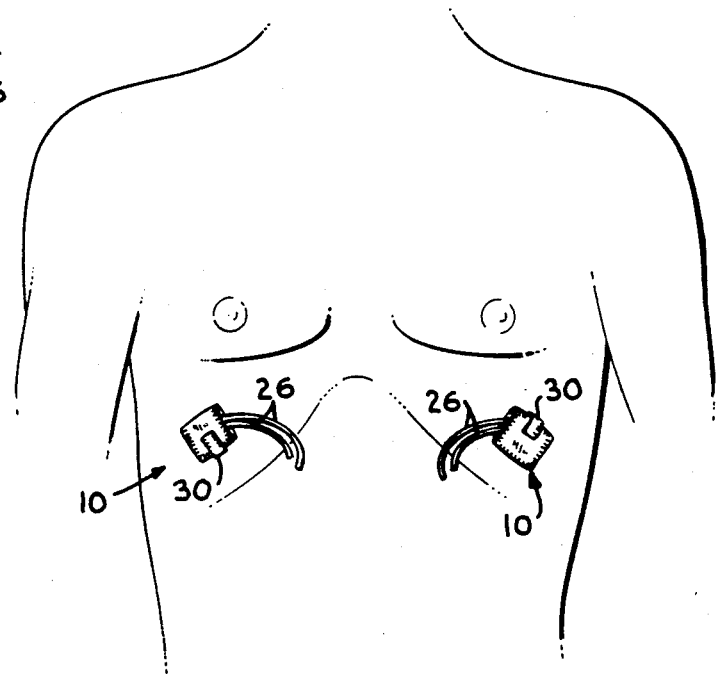
FIG. 4 is a perspective view of two closed dressings in place against a patient s chest with the ends of the pacemaker wires protruding from the patient's body and enclosed by the surgical dressings of the present invention.

The envelope or booklet 10 would be taped to the patient's chest by means of transparent tape (not shown), preferably with the fasteners 30 toward the patient's body rather than facing out as shown in FIG. 4, so that the tape and dressing 10 could be lifted and removed as a unit and the wires 26 extracted from the respective pouches or pockets 24 without the necessity of undoing the fastener 30.

Figure 5:
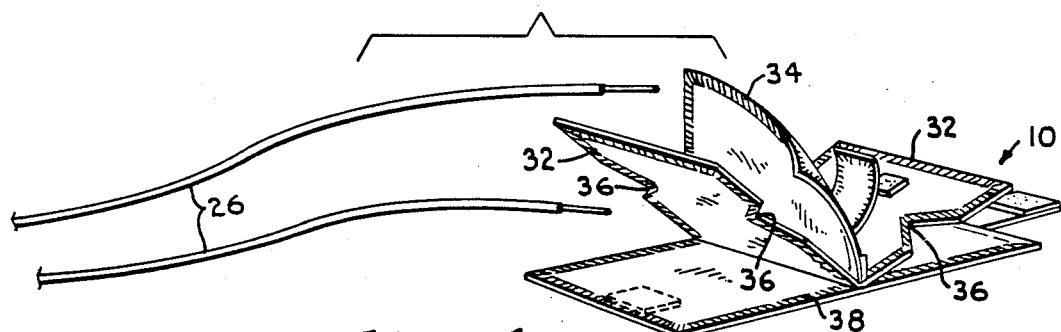
FIG. 5 is a perspective view of an alternative embodiment of a dressing disposed in booklet form with its inner pages open to reveal details of construction and placement of the end fastening devices.

FIG. 5 shows an alternative embodiment of the dressing 10, the leads or wires 26 being separated in this embodiment by inner compartments or pages 32 with an additional divider page 34 serving to further divide the negative and positive wires 26. In this embodiment the wires 26 are wrapped around the pages 32 as shown in FIG. 6, using notches 36 in the top and bottom edges 38 of pages 32 as guides or holders and then, securing, the leads 26 by means of fasteners 40 with VELCRO fastener tabs 42 which are attached medially to pages 32 and close horizontally across the leads 26 where they are mated with VELCRO fastener tabs 44.

Figure 6:
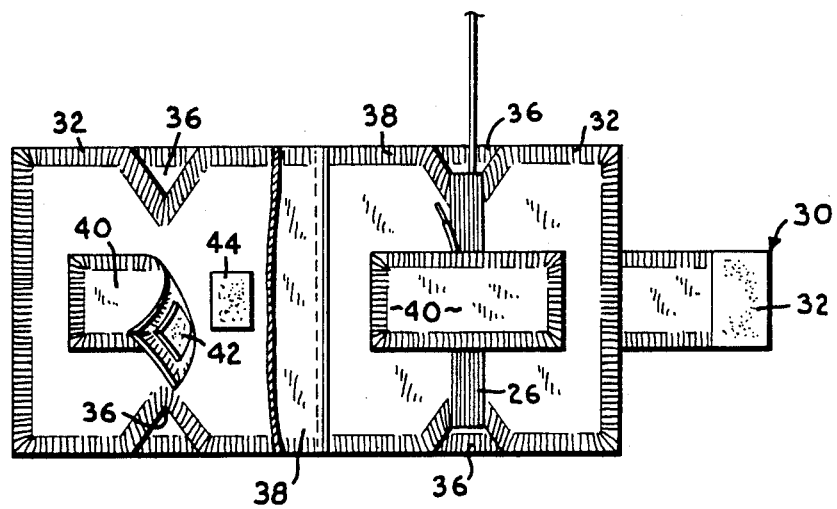
FIG. 6 is a top plan view of the embodiment of FIG. 5 showing the inner pages flat against the covers and pacemaker wire coiled around the right page of the booklet and secured by a fastener, with the left page revealing an inner velcro fastener in open position and an additional velcro fastener in open position extending from the right-hand cover.
Figure 7:
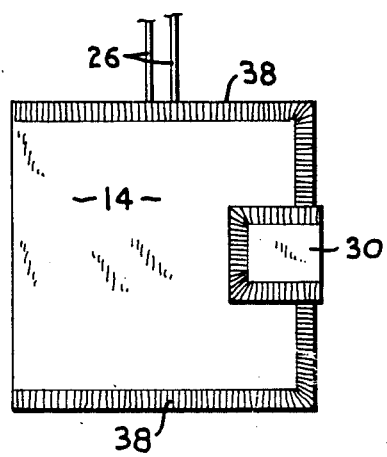
FIG. 7 is a top plan view of the dressing of FIGS. 5 and 6 closed, with the booklet shut and the end fastener in place to secure the wrapped pages.

The dressing 10 of FIG. 6 is substantially similar to the dressing 10 of FIG. 3 when the covers are closed left to right, but the leads 26 will be extending from the top or bottom edges 38 of dressing 10 rather than the corner when the dressing 10 is in closed position. The probes 28 can be tucked under laps of the wrapped leads 26.

Figure 8:
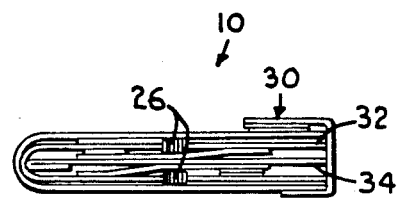
FIG. 8 is an edge elevation of the closed dressing of FIG. 7, each notched page being wrapped with a pacemaker wire in the sandwich or booklet configuration shown.

When viewed from the edge as in FIG. 8, the dressing 10 of FIG. 6 can be seen with the wires 26 in wrapped position and the divider page 34 of FIG. 5 shown sandwiched between the pages 32.

The dressings 10 may be made of gauze, cheesecloth or other lightweight, non-allergenic material and may be taped to a patient's chest by use of transparent tape (not shown) of sufficient size to cover the entire dressing 10. If the wires 26 of the dressing 10 must be removed from the dressing 10 for attachment to an external pacemaker or other monitoring machine, the tape and dressing 10 can be lifted from the patient's chest and the wires 26 extracted without wasted effort or delay.

All edges of the dressing 10 may be sewn to eliminate raveling, but as is apparent from the drawings, the preferred embodiment of FIGS. 1 and 2 requires less stitching and does not employ inner fasteners 40 and thus is less expensive to manufacture than the embodiment of FIGS. 5 and 6.

Having thus described the invention, what is claimed as new and desired to be secured by Letters Patent is:

1. In a dressing:
   (a) a booklet having a pair of outer cover pages and a pair of inner pages defining a corresponding pair of pocket compartments therebetween for receiving a corresponding pair of electrical leads extending from a patient,
   (b) means in said booklet establishing a line of fold about which the booklet may be opened or closed,
   (c) said pocket compartments being disposed on opposite sides of said line of fold when the booklet is opened, said inner pages separating each pocket compartment from the other when the booklet is closed, whereby the leads may be inserted into the pocket compartments when the booklet is open and maintained independent from each other upon closure of the booklet,
   (d) fastening means on said booklet for maintaining the same in the closed condition,
   (e) said outer cover pages being formed by a rectangular piece of material divided by said line of fold, so that said outer cover pages are substantially identical in size when said booklet is in the closed condition,
   (f) said inner pages formed by a rectangular piece of material substantially identical in size to said piece of material forming said outer cover pages, and
   (g) said outer cover pages and inner pages being attached by stitching on said line of fold and adjacent to top and bottom edges of said inner and outer joined pages whereby said compartment pockets are presented which are accessible from the sides.

2. A dressing booklet for receiving portions of a pair of electrical leads, which includes:
   (a) an outer cover piece of material forming a pair of outer cover pages each having a respective top edge, bottom edge and side edge,
   (b) an inner piece of material forming a pair of inner pages each having a respective top edge, bottom edge and side edge,
   (c) a fold line extending between said inner and outer page top and bottom edges intermediate said inner and outer page side edges,
   (d) fold line stitching interconnecting said inner and outer material pieces along said fold lines,
   (e) top and bottom stitching interconnecting said inner and outer material pieces along said top and bottom page edges respectively,
   (f) a pair of pocket compartments each formed by a respective, corresponding inner and outer page and open at the side edges thereof, each said pocket compartment being adapted to receive a respective electrical lead,
   (g) said booklet having open and closed conditions and being foldable therebetween along said fold lines, and
   (h) fastening means on said booklet for maintaining the same in its closed condition.

3. The dressing as claimed in claim 2, wherein said fastening means includes a hook-and-loop fastener.

4. The dressing as claimed in claim 2, wherein said booklet is made of gauze.

5. The dressing as claimed in claim 2, wherein said booklet is made of cheesecloth.

6. The dressing as claimed in claim 2, wherein said material pieces comprise woven fabric.

7. In a dressing:
   (a) a booklet having a pair of outer cover pages and a pair of inner pages associated with a corresponding pair of pocket compartments therebetween for receiving a corresponding pair of electrical leads extending from a patient,
   (b) means in said booklet establishing a line of fold about which the booklet may be opened or closed,
   (c) said pocket compartments being disposed on opposite sides of said line of fold when the booklet is opened,
   (d) a divider page separating each pocket compartment from the other when the booklet is closed, whereby the leads may be inserted into the pocket compartments when the booklet is open and maintained independent from each other upon closure of the booklet;
(e) fastening means on said booklet for maintaining the same in the closed condition,
(f) said outer cover pages being formed by a rectangular piece of material divided by said line of fold, so that said outer cover pages are substantially identical in size when said booklet is in the closed condition,
(g) said inner pages being formed by a rectangular piece of material substantially identical in size to said piece of material forming said outer cover pages,
(h) said outer cover pages, inner pages and divider page being attached by stitching on said line of fold,
(i) each of said inner pages being notched at its top and bottom edges, and
(j) each said inner pages being adapted to receive a respective electrical lead wound around it and passing through said notches.

* * * * *